United States Patent [19]

Berke et al.

[11] Patent Number: 4,581,351

[45] Date of Patent: Apr. 8, 1986

[54] COMPOSITION OF MATTER CONTAINING IMIDAZOLIDINYL UREA AND PYRITHIONE AND ITS DERIVATIVES

[75] Inventors: Philip A. Berke, Madison; William E. Rosen, Summit, both of N.J.

[73] Assignee: Sutton Laboratories, Inc., Chatham, N.J.

[21] Appl. No.: 610,429

[22] Filed: May 15, 1984

Related U.S. Application Data

[63] Continuation of Ser. No. 444,234, Nov. 23, 1982, abandoned.

[51] Int. Cl.[4] .................. A61K 7/06; A23L 3/34; A01N 43/50; A01N 52/02
[52] U.S. Cl. .................. 514/188; 252/47.5; 252/106; 252/107; 424/63; 424/70; 424/DIG. 5; 426/335; 426/532; 514/345; 514/347; 514/390; 514/844; 514/845; 514/846; 514/847; 514/848
[58] Field of Search .................. 424/245, 263, 273 R, 424/63, 70, DIG. 5; 514/844–848, 188, 345, 347, 390; 252/106, 107, 47.5; 426/335, 532

[56] References Cited

U.S. PATENT DOCUMENTS

| 2,745,826 | 5/1956 | Semenoff et al. | 260/96.5 |
| 3,248,285 | 4/1966 | Berke | 424/71 |
| 4,089,945 | 5/1978 | Brinkman et al. | 424/164 |

FOREIGN PATENT DOCUMENTS 761171 11/1956 United Kingdom .

OTHER PUBLICATIONS

*Cosmetics & Toiletries,* vol. 96, No. 3, p. 87, Sodium and Zinc Omadine Antimicrobials as Cosmetic Preservatives, by Nelson & Hyde (1981).
Rosen et al; J. Soc. Cosmet. Chem., 28, pp. 83–87 (Feb. 1977).
Rosen et al, J. Soc. Cosmet. Chem. 24, pp. 663–675 (Sep. 1973).

*Primary Examiner*—Allen J. Robinson
*Attorney, Agent, or Firm*—Bacon & Thomas.

[57] ABSTRACT

A composition of matter comprising a major part of imidazolidinyl urea and a minor part of pyrithione and/or one or more derivatives of pyrithione is disclosed. The composition exhibits synergistic anti-microbial activity.

11 Claims, No Drawings

COMPOSITION OF MATTER CONTAINING IMIDAZOLIDINYL UREA AND PYRITHIONE AND ITS DERIVATIVES

This application is a continuation of application Ser. No. 444,234, filed Nov. 23, 1982, now abandoned.

BACKGROUND OF THE INVENTION

The present invention is directed to a composition of matter which exhibits synergistic activity against contaminating micro-organisms.

Pyrithione, also identified as 2-mercaptopyridine-1-oxide and 1-hydroxypyridine-2-thione and given CAS registry numbers 1121-30-8 and 1121-31-9, and its derivatives are known to be active against a variety of microorganisms. They, therefore, have been used in a variety of products to inhibit contamination by micro-organisms including cosmetics, lubricants, and water-based paints. The most commonly used derivatives of pyrithione are the alkali metal and heavy metal salts, principally the sodium and zinc salts. See, Nelson and Hyde, "Sodium and Zinc Omadine ® Antimicrobials as Cosmetic Preservatives", *Cosmetics & Toiletries*, Vol. 96, No. 3, p 87. However, other derivatives such as pyrithione disulfide and the magnesium sulfate adduct thereof have also been proposed as antimicrobial agents. Further details concerning the manufacture and use of pyrithione and its derivatives are found in U.S. Pat. No. 2,745,826 and British Patent Specification No. 761,171, the disclosures of which are hereby incorporated by reference.

Imidazolidinyl urea is the name given to a bacteriocidal compound prepared as described in Example IV of U.S. Pat. No. 3,248,285 (and hereby incorporated by reference) and has been given the CAS registry number 39236-46-9. This compound has been widely used to preserve cosmetics, agricultural products and foodstuffs, paints, lubricants, plastics and textiles from bacteria.

The present invention is predicated upon the discovery that a composition of matter based on the combination of imidazolidinyl urea and pyrithione and/or its derivatives exhibits synergistic activity against the micro-organism *C. albicans*, a commonly occurring and problematic microbial. The composition, thus, provides a new and effective means for protecting perishable products from the harmful effects of contaminating micro-organisms.

SUMMARY OF THE INVENTION

The composition of the invention comprises a major part of imidazolidinyl urea and a minor part of pyrithione and/or its derivatives. By the term major part is meant more than 50% by weight based upon the total weight of the imidazolidinyl urea and pyrithione components of the composition. Conversely, the term minor part means less than 50% by weight based upon the total weight of the imidazolidinyl urea and pyrithione components.

Particularly preferred compositions are those containing sodium or zinc pyrithione and imidazolidinyl urea.

The composition of the invention may be used to preserve a variety of liquid and solid products from microbial contamination including, but not limited to, lotions, creams, soaps, shampoos and hair conditioners, lubricants, plastics, agricultural products and foodstuffs, pharmaceutical products and medicaments.

DETAILED DESCRIPTION OF THE INVENTION

Since imidazolidinyl urea and pyrithione and its derivatives can be manufactured as powdered solids, the composition of the invention may be prepared as a powder by simply mixing the individual components together in the appropriate proportions. Alternatively, aqueous solutions can be prepared from imidazolidinyl urea, which is highly water soluble and the pyrithione derivatives which are also water soluble, such as sodium pyrithione. Aqueous dispersions may be prepared from non-water soluble pyrithiones, such as zinc pyrithione. Other solvents can be used to prepare liquid formulations of the composition as, for example, propylene glycol. Of course, the choice of solvent will depend upon the solubility characteristics of the particular pyrithione(s) used in the composition.

As shown in the following Table, the combination of a pyrithione and imidazolidinyl urea exhibits synergistic antimicrobial activity, in a challenge test using *Candida albicans* (ATCC 10231):

| Test Solution | Concentration | Results on Subculture after 72 hour Incubation Period |
| --- | --- | --- |
| Imidazolidinyl urea | 0.3% | + |
|  | 0.6% | + |
| Sodium pyrithione | 0.005% | + |
|  | 0.006% | + |
|  | 0.007% | + |
|  | 0.008% | + |
|  | 0.010% | + |
| Imidazolidinyl urea (0.3%) plus Sodium pyrithione (0.005%) |  | 0 |

+ representing growth of microorganisms on subculture (i.e., microbial survival in test solution)
0 representing no growth on subculture (i.e., complete kill in test solution)

The challenge test was conducted as follows:
1. 4.5 ml of the undiluted compound was placed into a 16×150 mm test tube.
2. 0.5 ml of a 24 hour Trypticase Soy Broth (TSB) culture was added to the compound.
3. The challenged compound was allowed to sit at room temperature for 72 hours, after which a count was made on the sample to recover the viable cells, using standard pour plate procedure and trypticase soy agar pour plates. The remainder of the sample was added to 100 ml of TSB for a sterility test.
4. All subculture media were incubated at 35° C. for 48 hours and then observed for growth.
5. All negative media were challenged with a low number of organisms to assure that the media was growth-promoting.

The challenge test demonstrates that although 0.6% imidazolidinyl urea or 0.01% sodium pyrithione failed to kill *C. albicans*, a mixture of half of each, i.e., 0.3% imidazolidinyl urea and 0.005% sodium pyrithione achieved a complete kill.

The actual microbial counts make clear that the combination of imidazolidinyl urea and pyrithione is indeed synergistic. All challenges involved starting (challenge) concentrations of approximately $10^6$ micro-organisms per ml of test solution. After 72 hours in either 0.3% imidazolidinyl urea or 0.005% sodium pyrithione, the concentration of micro-organism was unchanged within experimental error, certainly less decrease than a factor of 10. The combination test solution would therefore be expected to have, after 72 hours, concentrations of micro-organism either unchanged or at most decreased by a factor of 20. Yet the mixture of imidazolidinyl urea and sodium pyrithione, in fact, reduced the concentration of micro-organism from $10^6$ to 0—a factor of 1,000,000.

The synergistic activity of the composition of the invention makes it a highly attractive preservative for a wide variety of products which are susceptible to contamination by micro-organisms.

The composition of the invention is particularly attractive for use in cosmetic products. It is readily incorporated in aqueous-based products, emulsions and solid formulations. Moreover, because of its synergistic activity, the composition is effective in applications where the individual components are by themselves ineffective. Typical cosmetic products effectively preserved by the composition of the invention are creams, lotions, shampoos, hair conditioners, eyeliners, and other eye make-up products.

In addition to cosmetics, the composition of the invention may be used to preserve almost any substance which is susceptible to microbial contamination including foodstuffs and pharmaceutical formulations. While effective amounts will vary depending upon the product being preserved, generally the amount of the composition incorporated into a product will not exceed 1.0% by weight. In this amount, the pyrithione component(s) will generally be present in an amount from about 0.025 to 0.1%, the remainder of the composition being imidazolidinyl urea.

The invention, therefore, also relates to a method of preserving products susceptible to microbial contamination by incorporating therein an effective amount of the composition of the invention, and the products so preserved.

While the invention has now been described in terms of certain preferred embodiments, one skilled in the art will readily appreciate that various modifications, changes, omissions and substitutions may be made without departing from the spirit thereof. It is intended, therefore, that the present invention be limited solely by the scope of the following claims.

We claim:

1. A composition for treating microbial contamination by the micro-orgaism *C. albicans* in a susceptible product comprising an anti-microbial effective amount of about 0.3%, by weight, imidazolidinyl urea and about 0.005%, by weight, of a pyrithione compound selected from the group consisting of pyrithione, alkali salts of pyrithione, heavy metal salts of pyrithione and mixtures thereof.

2. The composition of claim 1, wherein said pyrithione compound is sodium pyrithione.

3. The composition of claim 1, wherein said pyrithione compound is zinc pyrithione.

4. The composition of claim 1, 2, or 3, wherein said product is a cosmetic product.

5. The composition of claim 1, 2, or 3, wherein said product is an agricultural product.

6. The composition of claim 1, 2, or 3, wherein said product is a foodstuff.

7. The composition of claim 1, 2, or 3, wherein said product is a pharmaceutical product or a medicament.

8. A method of preserving a product susceptible to microbial cotamination by the micro-organism *C. albicans* comprising incorporating in said product an anti-microbial effective amount of about 0.3%, by weight, imidazolidinyl urea and about 0.005%, by weight, of a pyrithione compound selected from the group of pyrithione, alkali salts of pyrithione, heavy metal salts of pyrithione and mixtures thereof.

9. The method of claim 8, wherein said pyrithione compound is sodium pyrithione.

10. The method of claim 8, wherein said pyrithione compound is zinc pyrithione.

11. The method of claim 8, 9, or 10, wherein said product is selected from the group consisting of cosmetic products, agricultural products, foodstuffs and pharmaceutical products and medicaments.

* * * * *